United States Patent [19]

Mechoulam et al.

[11] Patent Number: 4,876,276

[45] Date of Patent: Oct. 24, 1989

[54] (3S-4S)-7-HYDROXY-Δ⁶-TETRAHYDROCAN-NABINOLS

[75] Inventors: Raphael Mechoulam; Jeffery J. Feigenbaum, both of Jerusalem; Naphtali Lander, Tel-Aviv, all of Israel; Morris Srebnik, Lafayette, Ind.

[73] Assignee: Yissum Research Development Co. of The Hebrew University of Jerusalem, Jerusalem, Israel

[21] Appl. No.: 112,705

[22] Filed: Oct. 26, 1987

[30] Foreign Application Priority Data

Oct. 24, 1986 [IL] Israel ........................................ 80411

[51] Int. Cl.⁴ ..................... A61K 31/35; C07D 311/80
[52] U.S. Cl. .................................... 514/454; 549/390; 549/391
[58] Field of Search ................. 549/390, 391; 514/454

[56] References Cited

U.S. PATENT DOCUMENTS

| | | | |
|---|---|---|---|
| 3,873,576 | 3/1975 | Petrizilka | 549/390 |
| 4,075,230 | 2/1978 | Archer et al. | 549/391 |
| 4,102,902 | 7/1978 | Archer et al. | 549/391 |
| 4,133,819 | 1/1979 | Johnson | 549/390 |
| 4,179,517 | 12/1979 | Mechoulam et al. | 549/390 |

OTHER PUBLICATIONS

R. Mechoulam, Ed., Cannabinoids as Therapeutic Agents, CRC Press, Boca Baton, Fl., 1986, pp. 66–67, 79, 115.

*Primary Examiner*—Nicky Chan
*Attorney, Agent, or Firm*—Browdy and Neimark

[57] ABSTRACT

The invention relates to novel (3S,4S)-7-hydroxy-Δ⁶-tetrahydrocannabinol homologes and derivatives, essentially free of the (3R,4R) form and to pharmaceutical compositions which have a potent analgetic, antiemetic and antiglaucoma effect, which compositions contain an effective dosage of a compound of this type. The novel pharmaceutical compositions are practically devoid of the undesired side effects of the (3R,4R) type compounds, such as cannabimimetic psychotropic effects. The pharmaceutical compositions are of special utility in cases of acute and of chronic pain. The invention also relates to a process for the production of the above defined novel compounds.

10 Claims, No Drawings

(3S-4S)-7-HYDROXY-Δ⁶-TETRAHYDROCAN-NABINOLS

FIELD OF THE INVENTION

The invention relates to pharmaceutical compositions which are potent analgetic, antiemetic and antiglaucoma agents, and which are essentially free of cannabimimetic effects. The active ingredients of the novel pharmaceutical compositions are (3S,4S)-7-hyroxy-Δ⁶-tetrahydrocannabinol homologs and derivatives, essentially free of the (3R,4R)-form. The compounds are novel per se and are part of the invention.

BACKGROUND OF THE INVENTION

Cannabinoid compounds are known to have a wide variety of biological effect on mammals, many of which are of potential therapeutical value, see R Mechoulam Ed., Cannabinoids as Therapeutic Agents CRS Press, Boca Baton, Fla. 1986. The drawback of many of the compounds which have such potential are side effects, and especially cannabimimetic effects which are highly undesirable.

According to the present invention the drawbacks have been overcome to a large extent, and the pharmaceutical compositions of the present invention are essentially devoid of such psychotropic side-effects. In R. Mechoulam et al, in The Cannabinoids: Chemical, Pharmacologic and Therapeutic Aspects, Academic Press, Ed. S. Agurell, W. L. Dewey and R. S. Willette, Orlando, Fla., 1984, pp 777–795, there have been published data on compounds which have a chirality which is opposite to that of the natural compounds, i.e. it is (3S,4S) rather than (3R,4R) of the natural compounds. An example of these compounds is the 1″,2″-dimethyl heptyl homolog of (3S,4S)-(+)-Δ⁶-THC.

This is a potentially valuable analgetic, however, it still causes some cannabimimetic side-effects, which may be due to the fact that the product may contain a minor quantity of the (3R,4R) enantiomer, which is strongly cannabimimetic.

As set out above, the present invention overcomes these drawbacks, and there is provided a synthetic route which makes possible to obtain the (3S,4S) enantiomers of the desired derivatives in essentially pure form, devoid of the undesired admixture of the (3R,4R) enantiomers.

SUMMARY OF THE INVENTION

The invention relates to compounds having the (3S,4S) configuration, and which are essentially free of the (3R,4R) enantiomer, which are of the formula:

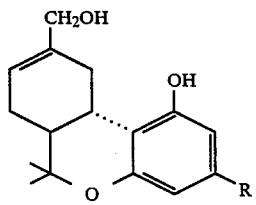

wherein R is selected from:
a. straight or branched alkyl of 6 to 12 carbon atoms;
b. a group of —O—R′, where R′ is straight or branched alkyl of 5 to 9 carbon atoms, or a straight or branched alkyl substituted at the terminal carbon atom by a phenyl group;
c. a group —(CH$_2$)$_n$—O—alkyl, where n is an integer of from 1 to 7 and the alkyl group contains 1 to 5 carbon atoms;

as well as to derivatives thereof, and to the mono- di- and tri-esters (of C$_1$ to C$_5$ fatty acids) of such compounds. There are provided novel pharmaceutical compositions which contain as active ingredient an effective quantity of a compound of the formula

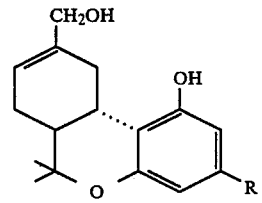

as well as functional derivatives thereof, which have the (3S,4S) configuration and which are essentially devoid of content of an appreciable contamination by the (3R,4R) enantiomer. The compositions of the invention are of value as analgetics, (in cases of either acute or chronic pain), antiemetics and as antiglaucoma agents. They are practically devoid of the undesired side-effects of the cannabimimetic type. Preferred compounds of the above formula, for the intended uses, are those wherein the alkyl group is as follows:

Compounds where the substituent in the 5-position is alkyl of 6 to 12 carbon atoms.

Compounds where such substituent is —O—R′, wherein the group R′ is an alkyl group (straight or branched), with 5 to 9 carbon atoms, or an alkyl-phenyl group, with 3 to 6 carbon atoms (straight or branched in the alkyl group), which is substituted at the terminal carbon with a phenyl group;

Compounds wherein the substituent in the 5-position is a —(CH$_2$)$_n$—O—alkyl, wherein n is 4 to 7, and where the alkyl group contains 1 to 5 carbon atoms. The designation of this type of compounds is as follows:

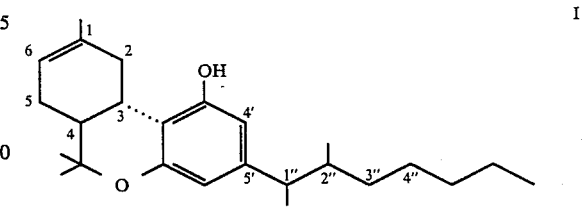

I

The invention provides a reaction sequence, which is illustrated for Compound IIa by the enclosed Reaction scheme I:

The present invention also relates to Compound V in crystalline form, which due to its crystallinity allows enantiometric purification, resulting in Compounds of type II, X and XI, which are the most potent compounds for use according to the invention, in pure enantiometic form.

According to a preferred embodiment of the invention, the compounds of the invention are administered as pharmaceutical compositions containing certain cupric salts, or these are administered separately.

The effective dosages for humans are within the range of from 0.1 to about 100 mg per unit dosage form.

They can be administered by injection, by oral route or by intracular topical application or in the form of suppositories.

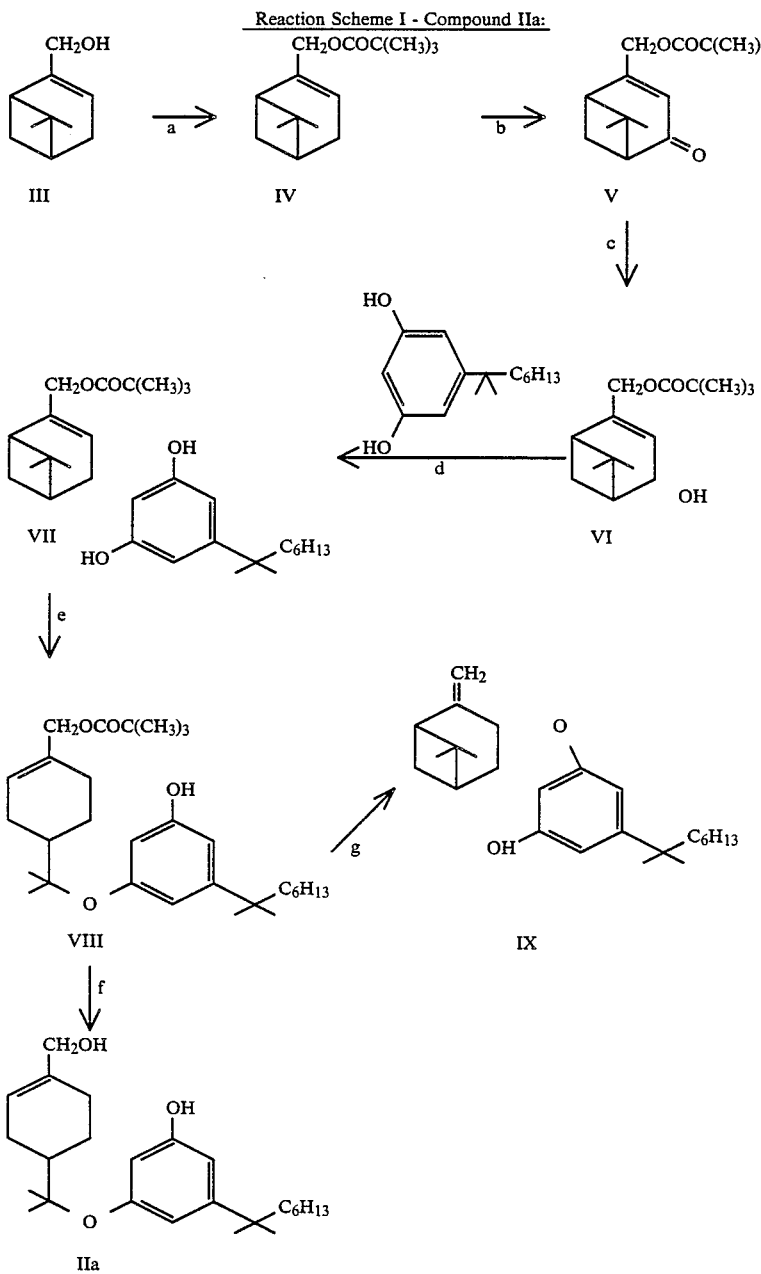

The starting material in the above synthesis, Compound III (+ form), is an oil which is difficult to obtain in absolute enantiometic purity. However, the intermediate V is crystalline and purifiable in high enantiomeric purity by crystallization, thus leading ultimately to IIa (3S,4S, +form), with absolute enantiometic purity.

A further salient feature of the above synthesis is the protection of the allylic alcohol in III by a bulky ester moiety. If a non-bulky ester is used i.e. an acetate, the ring closure to IIa (reaction f) does not take place as described. Instead, compound IX (reaction g) is obtained solely or predominantly. Compound IIa (+form) shows no cannabimimetic activity when tested by the ring test (ref 3 ), rotarod test (ref 4), and by drug discrimination tests in rats and pigeons (ref 5). By contrast, compound (IIa) shows potent analgetic activity in the hot plate test for mice and rats, acetic acid writhing test in mice, the rat tail immersion test (see Table 1-3), in reduction of intraocular pressure in rabbits (Table 4) and in prevention of vomiting in pigeons (Table 5)

Several novel features have to be pointed out: a: The activity in some tests (in particular analgesia) lasts for several days. This is of considerable therapeutic importance, in particular when used against chronic pain; b: Best activity in all tests is obtained when the solution administered contains cupric salts in molar concentrations equal to (or up to 5 times higher than) the molar concentration of the active cannabinoid.

SYNTHETIC EXAMPLES

Myrtenyl pivalate (IV)

(+) Myrtenol (20 g) $\alpha D+47.5°$ (neat) was dissolved in pyridine (100 ml). Pivaloyl chloride (32 g) was added at 0° over 30 min and the mixture was stirred at room temperature for 12 h. Ether (100 ml) and water-ice were added. The organic layer was washed with 10% HCl, then with a solution of sodium bicarbonate and then with brine. The dried organic layer was evaporated. On t.l.c. (10% ether in petroleum ether) a single spot was observed. The residue was purified by column chromatography on silica gel to give myrtenyl pivalate (IV) (11 g, $\nu$ max 1730 cm$^{-1}$, which was used in the next reaction without further purification.

Oxidation of myrtenyl pivalate (IV) with sodium chromate

Anhydrous sodium chromate (54 g, 0.33 mole) was added at 0° to a solution of (+) myrtenyl pivalate (IV) (34 g, 0.144 mole) in acetic acid (190 ml) and acetic anhydride (85 ml). The mixture was stirred at 35° under nitrogen for 72 h, cold water was added and the mixture was extracted with ether. The organic layer was washed with an aqueous solution of sodium hydrogen carbonate, dried and evaporated. The residue was chromatographed on silica gel (for dry column). Elution with 10% ether in light petroleum gave 4-oxo-myrtenyl pivalate (V) (14 g, 39%), m.p. 42-43 (from pentane); M+, 250; $\alpha D+156°$; $\lambda$ max 250 ($\epsilon$6000)nm; $\nu$max (CHCl$_3$) 1730 and 1670 cm$^{-1}$; $\delta$(CDCl$_3$) 1.03, 1.25 and 1.52 (me groups), 4.72 (CH$_2$—O), 5.84 (olefinic H). Anal. Calculated for C$_{15}$H$_{22}$O$_3$: C, 71.97%, H, 8.86%. Found: C, 72.30%; H, 8.26%.

4-Hydroxy myrtenyl pivalate (VI)

Compound (V) (0.75 g, 3 mmoles) was dissolved in dry tetrahydrofuran (130 ml)). A suspension of lithium hydrido-tri-t-butoxyaluminate (8.4 g, 33 mmol) in dry tetrahydrofuran (50 ml) was added over 20 min and the mixture was stirred at 0° C: under nitrogen for 3 h. Acetic acid (3 ml) and water (50 ml) were added and the stirring was continued for a further 0.5 h at room temperature. The mixture was filtered off and the precipitate was washed with chloroform. The chloroform solution was washed with water, dried and evaporated. 4-Hydroxy-myrtenyl pivalate (VI) (0.736 g, 97%) thus obtained showed one spot on t.l.c; M+, 352; $\alpha D+11.9$; $\nu$ max (CHCl$_3$) 3600 and 1730 cm$^{-1}$; $\delta$ (CDCl$_3$) 1.00, 1.13 and 1.29 (Me groups), 4.42 (4-H, 7-H), 5.58 (3-H).

Condensation of 4-hydroxy-myrtenyl pivalate (VI) with 5-(1,1-dimethyl heptyl)-resorcinol (+)-4-Hydroxy-myrtenyl pivalate (VI) (1.32 g, 5.24 mmol) in dry freshly distilled methylene chloride (50 ml) was added over a period of 30 min to a solution of 5-(1.1-dimethyl heptyl)resorcinol (1.24 g, 5.27 mmol) and dry anhydrous p-toluene sulfonic acid (270 mg) in dry methylene chloride (200 ml). The solution was left at room temperature, under nitrogen for 60 min washed with a saturated solution of sodium bicarbonate, dried and evaporated. The oil obtained was chromatographed on silica gel with 5% ether in petroleum ether as eluting solvent. The first compound to be eluted was compound (IX) (30 mg) m.p. 154°-155°, $\alpha D-169°$ (ethanol); $\delta$ (CDCl$_3$) 6.40 and 6.27 (aromatic H), 5.16 (m, C=CH$_2$), 3.79 (d, C-2H), 1.34, 1.21, 0.83 (methyl groups).

Analysis: C$_{25}$H$_{36}$O$_2$ requires: C, 81.47; H, 9.85%, Found: C, 81.85; H, 8.62%.

The second compound eluted is compound (VII), 60% yield a semi-solid, $\alpha D+75°$; $\nu$ max 1620 cm$^{-1}$; $\delta$ (CDCL$_3$) 6.21, 6.0, 4.61, 4.09, 1.39, 1.20, 1.18, 1.10, 0.82.

Synthesis of Compound (VIII)

Compound (VII) (2.7 g) was dissolved in dry methylene chloride (250 ml) (distilled over calcium hydride). Boron trifluorideetherate solution was stirred for 30 min under nitrogen. The solution was diluted with ether and washed with aqueous sodium bicarbonate. The organic phase was washed with water, dried over magnesium sulphate and the solvent was evaporated. The oil obtained (2.5 g) was chromatographed on silica gel. Elution was 5% ether in petroleum ether gave compound (IX) (300 mg). Elution with 12% ether in petroleum gave compound VIII (1.2 g) an oil, $\alpha D+131°$ (in ethanol); $\delta$ (CDCl$_3$) 6.39, 6.28, 5.78, 4.50, 1.40, 1.23, 1.20, 1.12, 0.84. In actual practice, the mixture obtained in this reaction is best directly submitted to the next reaction without purification. The reason is that IX and VIII are difficult to separate on chromatography while the products of the next reaction, namely IIa and IX, are easy to separate.

Synthesis of the 1,1-dimethyl heptyl homolog of 7-hydroxy-$\Delta^6$-tetrahydrocannabinol (IIa)

Compound (VIII) (0.132 g), $\alpha D+131°$ in dry ether (5 ml) was added to a suspension of lithium aluminum hydride (50 mg) in ether (30 ml). The mixture was boiled under reflux for 2 h. The excess of reagent was destroyed with saturated solution of sodium sulphate and HCl (1N), and the mixture was extracted with ether and washed with a solution of sodium bicarbonate. The extract was dried and evaporated to give (IIa) (0.112 g). After several crystallizations from pentane we obtained crystals. m.p. 141°-142°, $\alpha D+240°$ (in ethanol) $\delta$ (CDCl$_3$) 6.40, 6.24, 5.76, 4.09, 1.36, 1.16, 1.05, 085.

Anal. Calculated for C$_{25}$H$_{38}$O$_3$: C, 77.68%; H, 9.91%, Found: C 78.01%; H, 10.07%.

Additional Examples

Following the above route we have used numerous additional 5-substituted resorcinols in reaction d to obtain (after identical steps to those described above) the respective (3S,4S)-(+)7-hydroxy-$\Delta^6$-tetrahydrocannabinol analogs (of types II, X and XI). We have used, for example, as starting materials compounds of type XII:

5-(1,2-dimethyl heptyl)-resorcinol
5-(1,2-dimethyloctyl9 resorcinol
5-(1,2-dimethylhexyl) resorcinol
5-(1,1-dimethyl heptyl) resorcinol
5-(1-ethyl-2-methylpropyl) resorcinol
5-methylnonyl resorcinol
5-(1-methylnonyl) resorcinol
5-(1-methyloctyl) resorcinol
5-(1,2,4-trimethylhexyl) resorcinol
5-(1-ethylheptyl) resorcinol
leading to cannabinoids, type II.

We have also used ;b 5-substituted resorcinols in which the side-chain contains an ether (compounds of type XIII) leading to cannabinoids of type X. In (CH$_2$)$_n$ n can be 1 to 7. The alkoxy group in this case was OCH$_3$, OC$_2$H$_5$, OC$_3$H$_7$(n), OC$_4$H$_9$(n), OCH(CH$_3$)$_2$, OCH(CH$_3$)C$_2$H$_5$, OCH$_2$CH(CH$_3$)$_2$, etc.

A further group we used was based on 5 substituted resorcinols (type XIV) leading to cannabinoids of type XI. The C-5 groups in this case were:

O—CH(CH$_3$) (CH$_2$)$_4$CH$_3$
O—CH(CH$_3$)CH$_2$CH$_2$C$_6$H$_5$
O—CH(CH$_3$)CH$_2$CH$_2$CH$_2$C$_6$H$_5$.

TABLE 2
Effect of (+)7-OH-Δ$^6$-THC-DMH (IIa) with 5 × 10$^{-4}$ M CuCl$_2$) in the acetic acid (0.6%) induced writhing test in male mice*

| Dose mg/kg (s.c) | Writhings (per 20 min) |
|---|---|
| 25.0 | 23.1 |
| 5.0 | 17.7 |
| 2.5 | 7.7 |

STRUCTURES

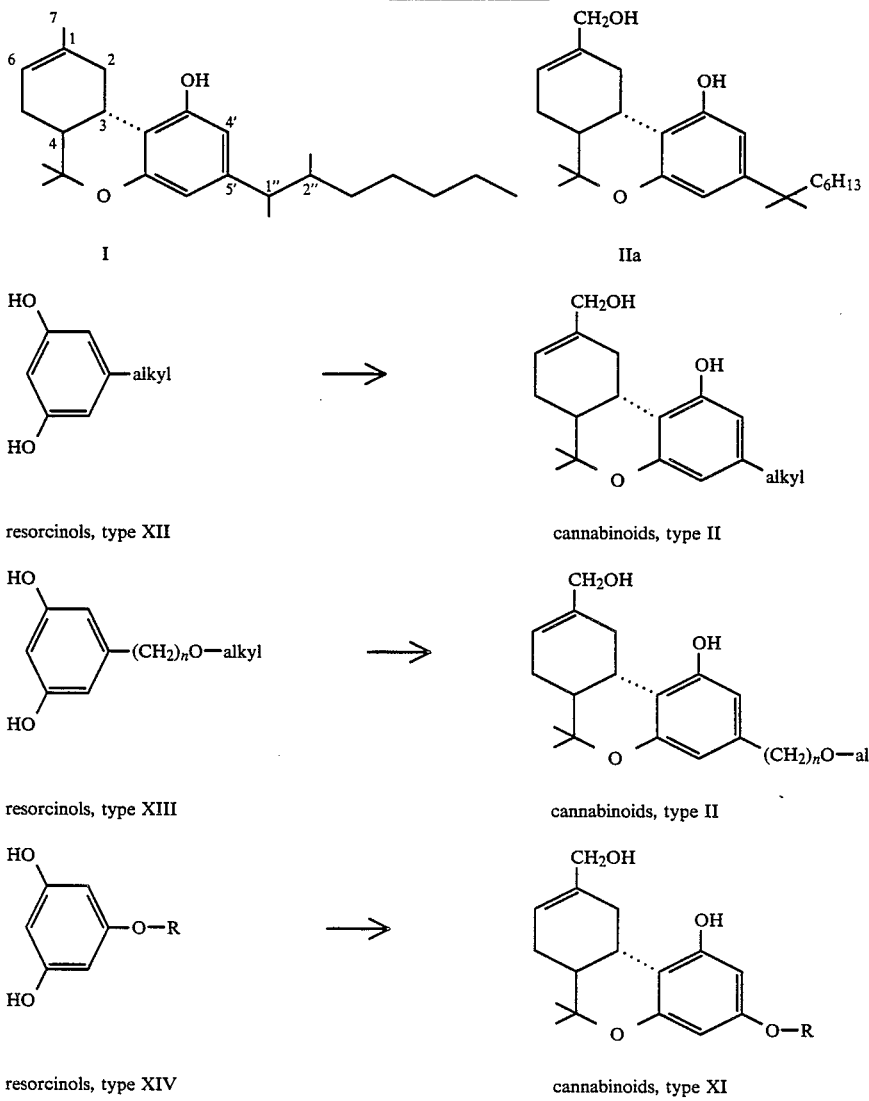

TABLE 1
Effect of (+)7-OH-Δ$^6$-THC-DMH (IIa) (with 5 × 10$^{-4}$ M CuCl$_2$) in the hot plate test in male mice*.

| Dose mg/kg,(s.c.) | Latency secs. |
|---|---|
| 2.5 | 30.0 |
| 1.0 | 24.8 |
| 0.5 | 25.2 |
| 0.25 | 23.8 |
| 0.05 | 11.0 |
| 0.0 | 7.3 |

*Compound dissolved in 0.5% EtOH and 0.5% Emulfor made up to injection volume (1.0 mg/kg body weight ml) with water.

| 0.5 | 12.2 |
|---|---|
| 0.25 | 14.1 |
| 0.05 | 19.3 |
| 0.025 | 32.5 |
| 0.0 | 33.2 |

*(same as in Table I).

TABLE 3
Effect of (+)-7-OH-Δ$^6$-THC-DMH (IIa) (with 5 × 10$^{-4}$ M CuCl$_2$). in the rat tail immersion test*

| Dose mg/kg (s.c.) | Response Latency (secs) |
|---|---|
| 2.5 | 24.7 |
| 1.0 | 20.2 |
| 0.25 | 16.8 |
| 0.05 | 4.0 |

TABLE 3-continued

Effect of (+)-7-OH-Δ⁶-THC-DMH (IIa) (with 5 × 10⁻⁴ M CuCl₂) in the rat tail immersion test*

| Dose mg/kg (s.c.) | Response Latency (secs) |
|---|---|
| 0.0 | 3.7 |

*(as in Table 1).

TABLE 4

Antiemetic efficacy of (+)7-OH-Δ⁶-THC-DMH (IIa) (with 5 × 10⁻⁴ M CuCl₂) against emesis induced by cis-platinum (7.5 mg/kg i.v.) in the pigeon*

| Dose of IIa mg/kg, s.c. | Relative amount of vomitus | Actual amount of vomitus | Frequency of response |
|---|---|---|---|
| 0 | — | 9.8 g | 100% (6/6) |
| 0.5 | 100% of control | 9.8 | 100% (6/6) |
| 1.5 | 25% of control | 2.4 | 80% (5/6) |
| 3.0 | 10% of control | 1.0 | 17% (1/6) |

*(Same as in Table 1)

TABLE 5

Effect of (+)-7-OH-Δ⁶-THC-DMH (IIa) (with 5 × 10⁻⁴ M CuCl₂) on reduction of intraocular pressure* in glaucomatic rabbits**

| Time of Treatment min. | Intraocular Pressure (mm Hg) |
|---|---|
| 0 | 29 |
| 30 | 20 |
| 60 | 22 |
| 90 | 21 |
| 360 | 22 |
| 1320 | 24 |

*Intraocular pressure induced by administration of the corticosteroid Betsovet as described in the literature.
**Dose: 0.2 ml of a 0.6% solution in light mineral oil administered onto the eye topically.

We claim:

1. A compound having the (3S,4S) configuration, which is essentially free of the (3R,4R) enantiomer, of the formula:

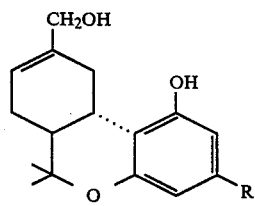

wherein R is selected from:
 a. straight or branched alkyl of 6 to 12 carbon atoms;
 b. a group —O—R', where R' is straight or branched alkyl to 5 to 9 carbon atoms, or a straight or branched alkyl substituted at the terminal carbon atom by a phenyl group;
 c. a group —(CH₂)$_n$—O—alkyl, where n is an integer of from 1 to 7 and the alkyl group contains 1 to 5 carbon atoms, wherein at least one of the —OH group can be esterified to provide an ester group having from 1 to 5 carbon atoms.

2. A pharmaceutical composition having analgetic, antiemetic, or antiglaucoma activity which contains as active ingredients a therapeutically effective quantity of a compound having the (3S,4S) configuration, and which is essentially free of the (3R,4R) enantiomer, which active compound is of the formula:

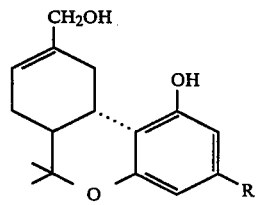

wherein R is selected from:
 a. straight or branched alkyl of 6 to 12 carbon atoms;
 b. a group —O—R', wherein R' is straight or branched alkyl of 5 to 9 carbon atoms, or a straight or branched alkyl substituted at the terminal carbon atom by a phenyl group;
 c. a group —(CH₂)$_n$—O-alkyl, where n is an integer of from 1 to 7 and the alkyl group contains 1 to 5 carbon atoms, wherein at least one of the —OH groups can be esterified to provide an ester group having from 1 to 5 carbon atoms, and wherein the active ingredient is in a quantity of from 0.1 mg to about 100 mg per unit dosage.

3. A composition according to claim 2, which further contains a quantity of a physiologically acceptable copper salt.

4. A method for treating a patient having glaucoma comprising administering to said patient an effective amount of a composition according to claim 2.

5. The method according to claim 4 wherein the composition is administered orally, by injection, or topically for intraocular use.

6. A method for relieving emesis in a patient suffering from emesis comprising administering to said patient an effective amount of a composition according to claim 2.

7. The method according to claim 6 wherein the composition is administered orally, by injection, or as suppositories.

8. A method for providing analgesia in a patient having need for analgesia comprising administering to said patient an effective amount of a composition according to claim 2.

9. The method of claim 8 wherein the composition is administered orally, by injection, or as suppositories.

10. The composition according to claim 2 wherein the active ingredient is combined with a pharmaceutically acceptable carrier so as to form a dosage form for oral use, for administration by injection, as suppositories, and for topical intraocular use.

* * * * *